US011406761B2

(12) United States Patent
Liscio et al.

(10) Patent No.: US 11,406,761 B2
(45) Date of Patent: Aug. 9, 2022

(54) INJECTOR DEVICE

(71) Applicant: SANOFI, Paris (FR)

(72) Inventors: Edward Liscio, Bridgewater, NJ (US); Tim Glässer, Mainz (DE); Matthias Rau, Wiesbaden (DE)

(73) Assignee: Sanofi, Paris (FR)

( * ) Notice: Subject to any disclaimer, the term of this patent is extended or adjusted under 35 U.S.C. 154(b) by 102 days.

(21) Appl. No.: 16/753,836

(22) PCT Filed: Oct. 29, 2018

(86) PCT No.: PCT/EP2018/079549
§ 371 (c)(1),
(2) Date: Apr. 6, 2020

(87) PCT Pub. No.: WO2019/086372
PCT Pub. Date: May 9, 2019

(65) Prior Publication Data
US 2020/0289754 A1    Sep. 17, 2020

(30) Foreign Application Priority Data

Oct. 30, 2017  (EP) ..................................... 17306488

(51) Int. Cl.
*A61M 5/20*     (2006.01)
*A61M 5/315*    (2006.01)

(52) U.S. Cl.
CPC ........ *A61M 5/2033* (2013.01); *A61M 5/3158* (2013.01); *A61M 5/31501* (2013.01);
(Continued)

(58) Field of Classification Search
CPC .............. A61M 5/3157; A61M 5/2033; A61M 2005/2073; A61M 2005/2026
(Continued)

(56) References Cited

U.S. PATENT DOCUMENTS

2005/0101919 A1    5/2005  Brunnberg
2009/0281496 A1   11/2009  Matusch
(Continued)

FOREIGN PATENT DOCUMENTS

CN    101583391    11/2009
CN    102630172     8/2012
(Continued)

OTHER PUBLICATIONS

International Preliminary Report on Patentability in Application No. PCT/EP2018/079549, dated May 5, 2020, 9 pages.
(Continued)

*Primary Examiner* — Bhisma Mehta
*Assistant Examiner* — Nidah Hussain
(74) *Attorney, Agent, or Firm* — Fish & Richardson P.C.

(57) ABSTRACT

An injector device comprising an elongate housing having a proximal end and a distal end, and configured to receive a container of medicament, a needle sleeve mounted within the housing and moveable between an extended position in which the needle sleeve at least partially extends from the distal end of the housing, and a retracted position in which the needle sleeve is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod. The release mechanism comprises a locking arm moveable between a locked position in which the locking arm is in cooperating engagement with the piston rod and prevents movement of the piston rod, and a release position in which the locking arm is out of engagement with the piston rod so that the piston rod is free to move longitudinally within the housing. The needle sleeve is (Continued)

configured such that movement of the needle sleeve from the extended position to the retracted position causes the locking arm to move from the locked position to the release position.

23 Claims, 13 Drawing Sheets

(52) U.S. Cl.
　　CPC ............... *A61M 2005/206* (2013.01); *A61M 2005/2013* (2013.01)

(58) Field of Classification Search
　　USPC ......................................................... 604/228
　　See application file for complete search history.

(56) References Cited

U.S. PATENT DOCUMENTS

| | | | |
|---|---|---|---|
| 2011/0196339 A1 | 8/2011 | Hirschel et al. | |
| 2012/0289907 A1 | 11/2012 | Veasey et al. | |
| 2012/0323177 A1* | 12/2012 | Adams | A61M 5/326 604/228 |

FOREIGN PATENT DOCUMENTS

| | | |
|---|---|---|
| CN | 102770173 | 11/2012 |
| CN | 103118723 | 5/2013 |
| CN | 103179996 | 6/2013 |
| CN | 105579084 | 5/2016 |
| CN | 106456899 | 2/2017 |
| DE | 102007008369 | 8/2008 |
| EP | 2605814 | 6/2013 |
| EP | 3222309 | 9/2017 |
| WO | WO 2006/111859 | 10/2006 |
| WO | WO 2010/017650 | 2/2010 |
| WO | WO 2011/039217 | 4/2011 |
| WO | WO 2011/101383 | 8/2011 |
| WO | WO 2011/109205 | 9/2011 |
| WO | WO 2012/022810 | 2/2012 |
| WO | WO 2012/030276 | 3/2012 |
| WO | WO 2015/150578 | 10/2015 |
| WO | WO 2015/160600 | 10/2015 |
| WO | WO 2017/089266 | 6/2017 |

OTHER PUBLICATIONS

International Search Report and Written Opinion in Application No. PCT/EP2018/079549, dated Jan. 3, 2019, 13 pages.

\* cited by examiner

A-A

INJECTOR DEVICE

CROSS-REFERENCE TO RELATED APPLICATIONS

The present application is the national stage entry of International Patent Application No. PCT/EP2018/079549, filed on Oct. 29, 2018, and claims priority to Application No. EP 17306488.2, filed on Oct. 30, 2017,the disclosures of which are incorporated herein by reference.

BACKGROUND

Injection devices, for example auto-injectors, typically have a sealed container of medicament, and a needle for injection of the medicament into a patient. In one type of device, the medicament container may comprise a medicament cartridge and the needle may be initially separated from the cartridge. An initial action moves the cartridge and needle together so that the needle pierces the cartridge. In another type of device, the medicament container may comprise a syringe containing a medicament and the needle may be secured to the syringe. In both cases, a plunger or piston within the cartridge or syringe can then be moved into the cartridge or syringe to dispense medicament through the needle for injection to a patient.

TECHNICAL FIELD

The present disclosure relates to an injector device for a medicament.

SUMMARY

In certain aspects, an injector device having a piston rod release mechanism is provided.

In one aspect, there is provided an injector device comprising an elongate housing having a proximal end and a distal end, and configured to receive a container of medicament, a needle sleeve mounted within the housing and moveable between an extended position in which the needle sleeve at least partially extends from the distal end of the housing, and a retracted position in which the needle sleeve is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod, the release mechanism comprising a locking arm moveable between a locked position in which the locking arm is in cooperating engagement with the piston rod and prevents movement of the piston rod, and a release position in which the locking arm is out of engagement with the piston rod so that the piston rod is free to move longitudinally within the housing, and wherein the needle sleeve is configured such that movement of the needle sleeve from the extended position to the retracted position causes the locking arm to move from the locked position to the release position. This may advantageously help provide a mechanism which is actuated upon movement of the needle sleeve.

According to a further aspect, there is provided an injector device comprising an elongate housing having a proximal end and a distal end, and configured to receive a container of medicament, a rear cap mounted to a proximal end of the housing and moveable between an extended position in which the rear cap at least partially extends from the distal end of the housing, and a depressed position in which the rear cap is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod, the release mechanism comprising a locking arm mounted on the rear cap and moveable between a locked position in which the locking arm is in cooperating engagement with the piston rod and prevents movement of the piston rod, and a release position in which the locking arm is out of engagement with the piston rod so that the piston rod is free to move longitudinally within the housing, and wherein the rear cap is configured such that movement of the rear cap from the extended position to the depressed position causes the locking arm to move from the locked position to the release position. This may advantageously help provide a mechanism which is actuated upon movement of the rear cap.

The locking arm may be configured to pivot between the locked position and the release position. Alternatively, the locking arm may be resiliently deflectable between the locked position and the release position, or may rotate between the locked position and the release position. The locking arm may be configured to rotate about an axis extending in a longitudinal direction of the housing between the locked and release position. This may advantageously help provide a compact and effective movement of release mechanism.

The piston rod may comprise a recess within which an end of the locking arm is received when the locking arm is in the locked position. Alternatively, or in addition, the piston rod may comprise a projection and the locking arm may comprise an aperture or recess within which the projection of the piston rod is received when the locking arm is in the locked position.

The release mechanism may comprise a securing member which engages the locking arm in the locked position and prevents movement of the locking arm into the release position. This may advantageously help prevent accidental release of the piston rod before intended actuation.

The release mechanism may be configured such that a contact portion of the release mechanism engages the securing member as the needle sleeve or rear cap moves to the retracted or depressed position respectively and moves the securing member out of engagement with the locking arm to allow the locking arm to move into the release position. This may advantageously help ensure an injection procedure is only initiated once the actuator is moved.

The securing member may comprise a deflectable post which is deformed out of engagement with the locking arm when the needle sleeve or rear cap is moved from the extended position to the retracted or depressed position respectively. This may advantageously help provide a reliable and cost-effective configuration of release mechanism.

The release mechanism may comprise a contact portion configured to engage the locking arm as the needle sleeve or rear cap moves to the retracted or depressed position respectively and moves the locking arm from the locked position to the release position. This may advantageously help provide a compact and reliable release mechanism with simple construction.

The locking arm may be configured to rotate about an axis extending in a longitudinal direction of the housing between the locked and release positions.

A support post may extend into the housing from the rear cap and the locking arm may be moveably connected to the support post. The locking arm may be pivotally connected to the support post, or may be a resiliently deflectable locking arm connected to the support post, or may rotatably connected to the support post. The locking arm may be configured to rotate about an axis extending in a longitudinal direction of the housing between the locked and release positions.

The locking arm may extend inwardly from a lateral side wall of the housing.

The locking arm may comprise a slot within which a portion of the needle sleeve is received when the needle sleeve is in the extended position to prevent movement of the locking arm from the locked position, and the needle sleeve may be configured such that movement of the needle sleeve to the retracted position renders the needle sleeve out of engagement with the slot to allow the locking arm to move to the release position.

The needle sleeve may be configured to engage the securing member as the needle sleeve moves to the retracted position and move the securing member out of engagement with the locking arm to allow the locking arm to move into the release position. The needle sleeve may comprise a contact portion configured to engage the securing member/deflectable post as the needle sleeve moves to the retracted position.

The rear cap may be configured such that the securing member is engaged as the rear cap moves to the depressed position and moves the securing member out of engagement with the locking arm to allow the locking arm to move into the release position. The housing may comprise a contact portion configured to engage the securing member/deflectable post as the rear cap moves to the depressed position.

The injector device may further comprise a needle unit at the distal end of the housing and may comprise an injection needle held in a needle holder. This may advantageously help provide a device which can be pre-assembled with an injection needle separately to provision of a reservoir of medicament.

The injector device may further comprise a container of medicament received within the housing between the piston rod and the distal end of the injector device. The container of medicament may comprise a cartridge of medicament, or may comprise a pre-filled syringe.

The release mechanism may comprise a plurality of locking arms. This may advantageously help provide a stable and symmetrical mechanism.

The locking arms may be formed integrally with housing. The locking arms may comprise resiliently deflectable members, pivotable members and/or rotatable members.

The or each securing member may comprise a chamfered contact edge. This may advantageously help provide a smooth release movement and reduce the force necessary to actuate the release mechanism.

The needle sleeve may comprise an end portion which is angled relative to axis of housing. This may advantageously help provide a smooth release movement and reduce the force necessary to actuate the release mechanism.

The or each securing member may comprise a projecting lug having an angled contact face.

The release mechanism and/or the locking arms may be moveable relative to the housing together with the rear cap.

Also provided is a method of operating an injector device, the device comprising an elongate housing having a proximal end and a distal end and configured to receive a container of medicament, a needle sleeve mounted within the housing and moveable between an extended position in which the needle sleeve at least partially extends from the distal end of the housing, and a retracted position in which the needle sleeve is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod, the release mechanism comprising a locking arm moveable between a locked position and a release position, the method comprising moving the needle sleeve from the extended position to the retracted position and thereby causing the locking arm to move from the locked position in which the locking arm is in cooperating engagement with the piston rod and prevents movement of the piston rod, to the release position in which the locking arm is out of engagement with the piston rod so that the piston rod is free to move longitudinally within the housing.

Also provided is a method of operating an injector device, the device comprising an elongate housing having a proximal end and a distal end and configured to receive a container of medicament, a rear cap mounted to a proximal end of the housing and moveable between an extended position in which the rear cap at least partially extends from the distal end of the housing, and a depressed position in which the rear cap is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod, the release mechanism comprising a locking arm moveable between a locked position and a release position, the method comprising moving the rear cap from the extended position to the depressed position and thereby causing the locking arm to move from the locked position in which the locking arm is in cooperating engagement with the piston rod and prevents movement of the piston rod, to the release position in which the locking arm is out of engagement with the piston rod so that the piston rod is free to move longitudinally within the housing.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

Figure 1A:
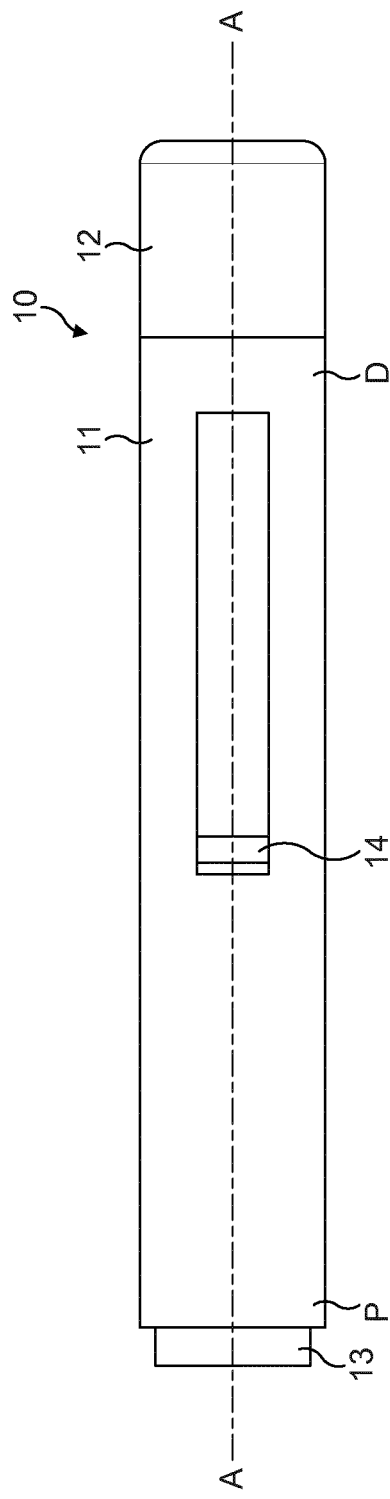
FIG. 1A is a schematic side view of an injector device, and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 3 ml. Another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml). Yet another device may comprise a pre-filled syringe within a housing of the device. The syringe may be fixed within the housing or may be moveable within the housing, for example from a retracted position to an operation extended position.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
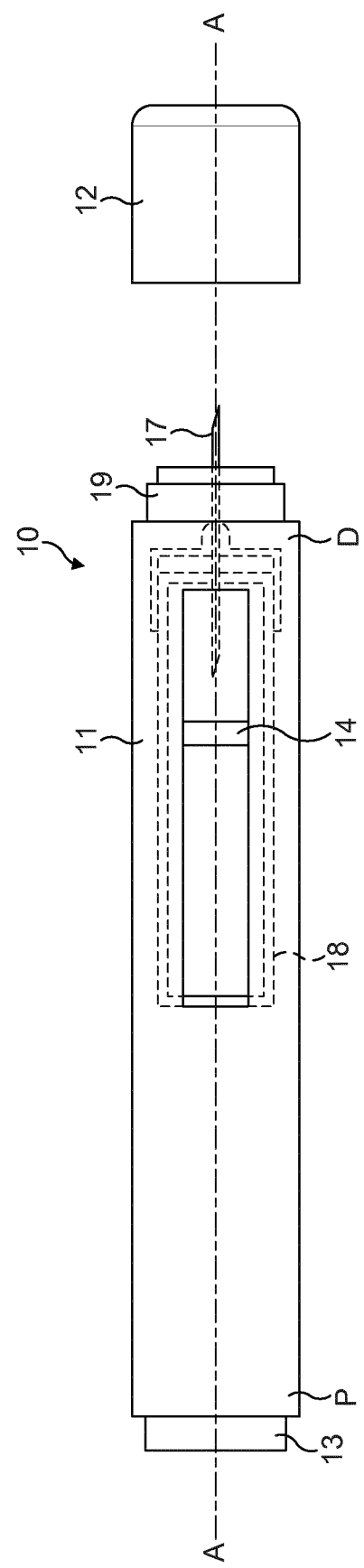
FIG. 1B is a schematic side view of the injector device of FIG. 1A, with the cap removed from the housing.

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge or pre-filled syringe that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

Figure 2:
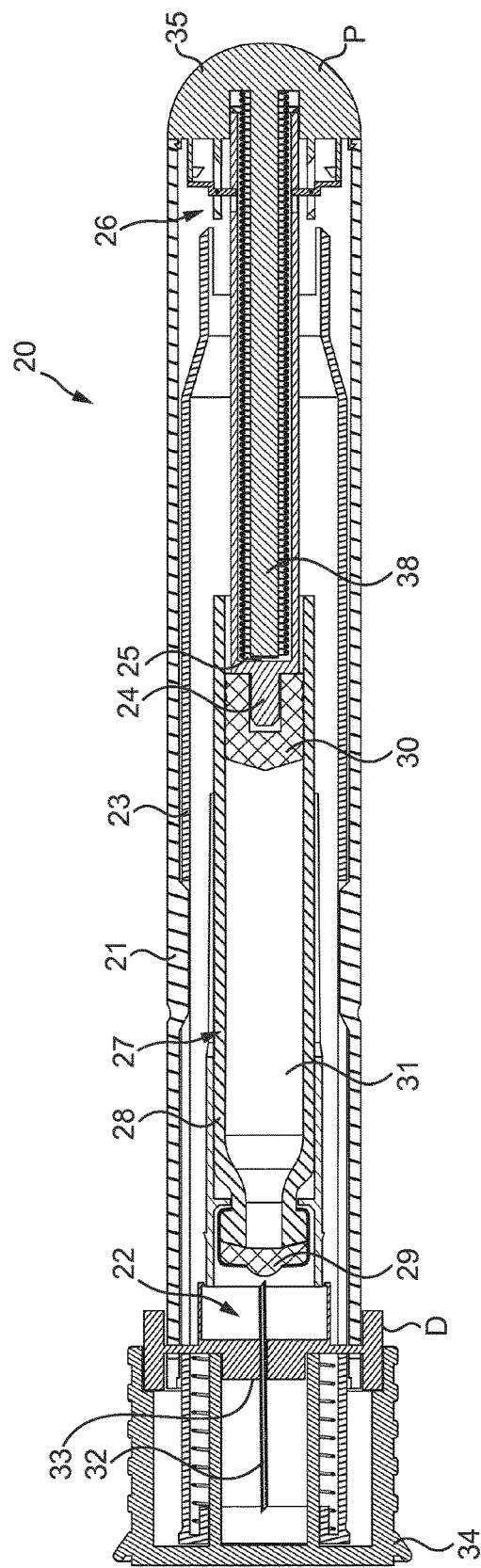
FIG. 2 is a side cross-sectional view of an injector device of a first embodiment.

FIG. 2 shows an injector device 20 of a first embodiment, comprising a housing 21, a needle unit 22, a needle sleeve 23, a piston rod 24, a piston spring 25, and a release mechanism 26.

The release mechanism 26 is configured to retain the piston rod 24 in an initial primed and locked position against the force of the piston spring 25, and upon activation, to release the piston rod 24 to be able to move under the force of the piston spring 25, as described in hereafter. In the exemplary embodiment shown in FIG. 2, the needle sleeve 23 comprises an actuator configured to operate the release mechanism 26, as described in more detail hereafter.

The injector device 20 comprises a distal end D and a proximal end P. The term "distal" refers to a location that is relatively closer to a site of injection, and the term "proximal" refers to a location that is relatively further away from the injection site. References hereinafter to "distal" and "proximal" are made in reference to the distal and proximal ends D, P respectively of the injector device 20. The housing 21 is configured to contain a medicament cartridge 27, as shown in FIG. 2. Such a medicament cartridge 27 comprises a cylindrical container 28 having a distal end which is sealed with a pierceable seal 29 and a proximal end which is sealed with a piston 30 disposed within the proximal end of the container 28. Medicament 31 is held within the container 28 between the piercable seal 29 and the piston 30.

The needle unit 22 comprises a needle 32 held in a needle holder 33 connected to the distal end of the housing 21. The needle sleeve 23 is connected to the housing 21 and configured to slide within the housing 21 in a longitudinal direction of the injector device 20. The needle sleeve 23 is moveable between a first, extended position and a second, retracted position. In the extended position, the needle sleeve 23 surrounds and shields the needle 32. In the retracted position, the needle 32 is exposed beyond the end of the needle sleeve 23. The needle sleeve 23 is shown in the extended position in FIG. 2. Also shown in FIG. 2 is an end cap 34 that initially covers the end of the needle sleeve 23 before use of the injector device 20.

Figure 3:
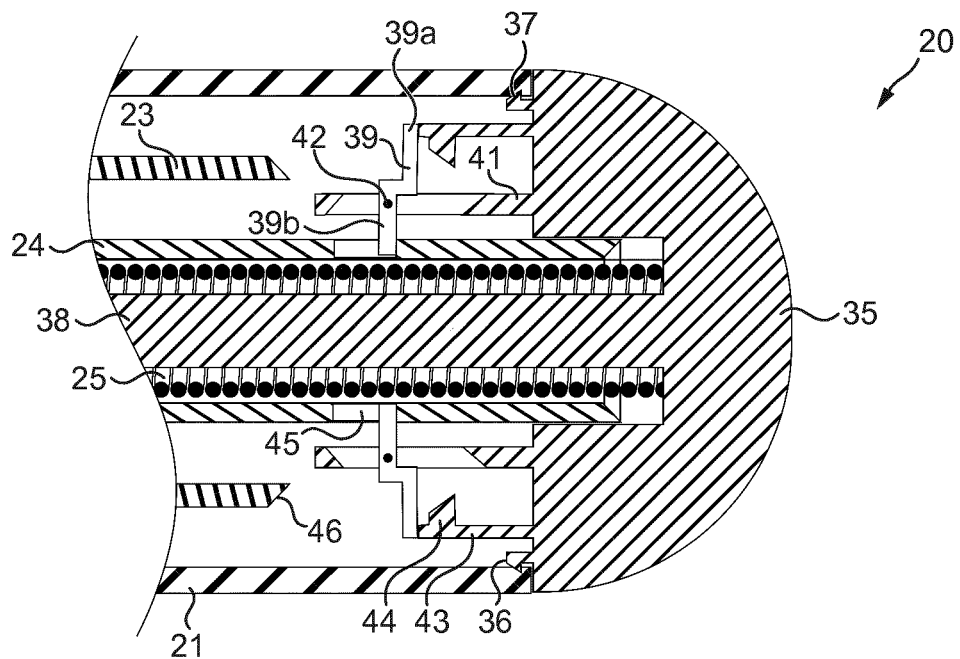
FIG. 3 is an enlarged cross-sectional view of a proximal end of the injector device of FIG. 2 illustrating the piston rod release mechanism in an initial, locked position, with the section view taken through the locking arm.

The proximal end of the injector device 20 includes a rear cap 35 which is retained in place by retaining arms 36 which engage with corresponding retaining portions 37 formed on the housing 21 (see FIG. 3 for example).

The piston spring 25 is disposed around an elongate projection 38 extending from the rear cap 35. The piston rod 24 has a hollow bore and is disposed over the elongate projection 38 and piston spring 25 such that the elongate projection 38 and piston spring 25 are received within the hollow bore of the piston rod 24. The piston spring 25 is in contact with the rear cap and is configured to urge the piston rod 24 in a distal direction of the injector device 20. When a medicament cartridge 27 is received within the injector device, the piston rod 24 is in contact with the piston 30 and is configured to drive the piston 30 within the container 28 once the piston rod 24 is released.

The piston rod 24 is initially held in locked, starting position, against the force of the piston spring 25 by the release mechanism 26. The release mechanism 26 is configured to be actuated to a released or unlocked position, to allow the piston rod 24 of move within the housing 21 under the force of the piston spring 25, as described in more detail below.

Figure 4:
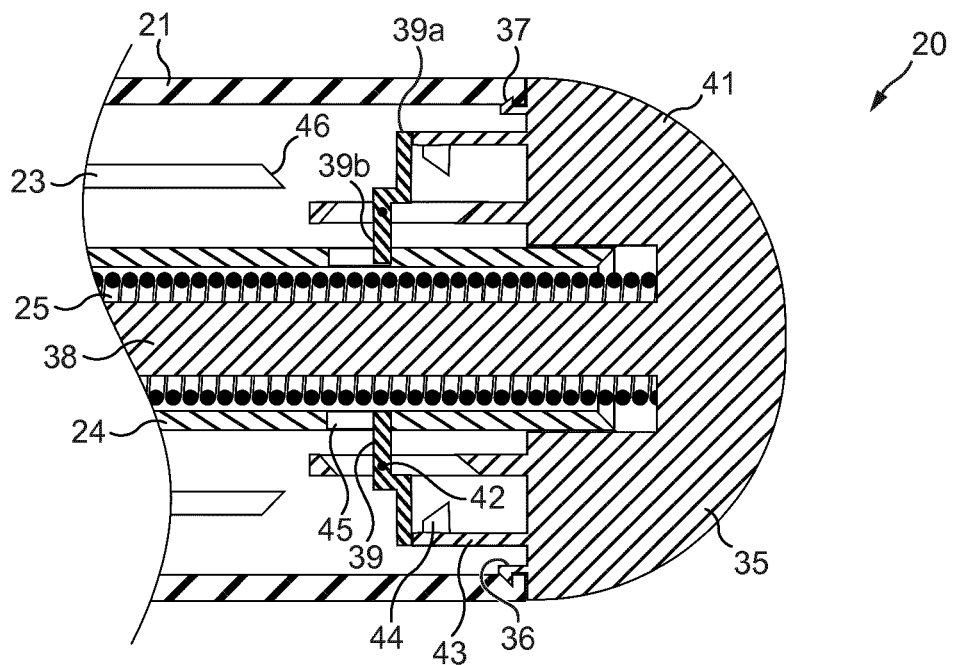
FIG. 4 is an enlarged cross-sectional view of the proximal end of the injector device of FIG. 2 illustrating the release mechanism in the initial, locked position as shown in FIG. 3, but with the section view taken through the deflectable locking members.
Figure 5:
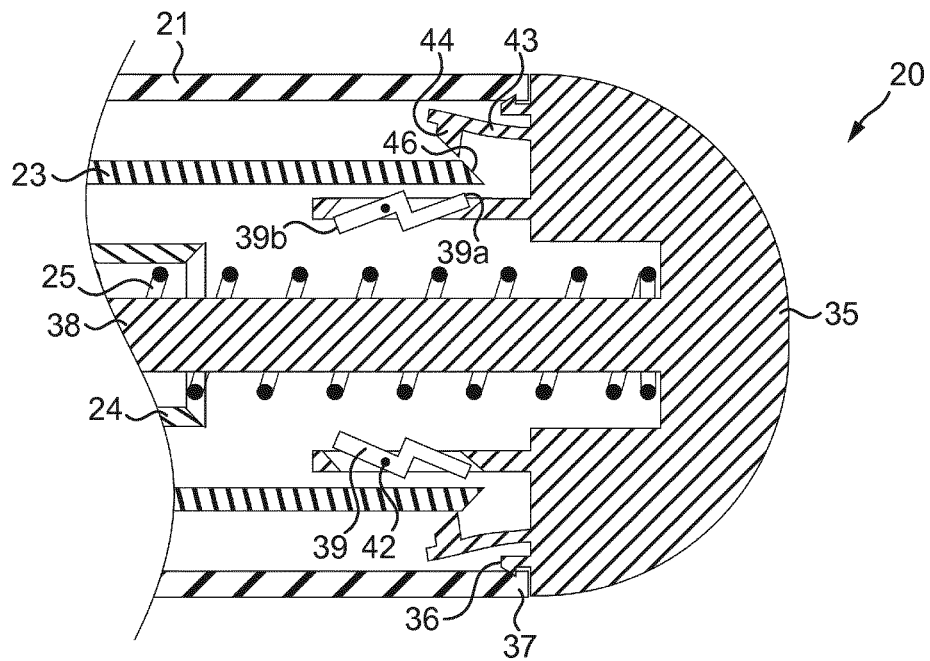
FIG. 5 is an enlarged cross-sectional view of the proximal end of the injector device of FIG. 2 with the section view taken through the deflectable locking members as in FIG. 4, but illustrating the release mechanism in an activated position.

The release mechanism 26 of the first embodiment can be seen in more detail in FIGS. 3 to 5. FIGS. 3 and 4 show the release mechanism 26 in the starting locked position, before a medicament delivery process is commenced. FIG. 5 shows the release mechanism 26 in the unlocked released position during a medicament delivery process.

The release mechanism 26 comprises a pair of locking arms 39 each mounted to a respective support post 41 at a pivot point 42 to enable the locking arms 39 to pivot between a locking position (shown in FIGS. 3 and 4) and a release position (shown in FIG. 5). The support posts 41 extend from the rear cap 35 and extend in a longitudinal direction of the housing 21, and are disposed on opposite sides, and on the outside, of the piston rod 24. Also extending from the rear cap 35 are deflectable arms 43. The deflectable arms 43 are moveable from a relaxed state (shown in FIGS. 3 and 4) to a deflected state (shown in FIG. 5). In the relaxed state, ends of the delectable arms 43 abut a respective first end 39*a* of the locking arms 39 when the locking arms 39 are in the locking position. The deflectable arms 43 in the relaxed state thereby act as securing members and prevent the locking arms 39 from rotating into the release position. The deflectable arms 43 further comprise a respective inwardly-projecting lug 44.

The piston rod 24 includes a recess 45 on opposite sides thereof and disposed radially aligned with each locking arm 39. When the locking arms 39 are in the locking position, a respective second end 39*b* of each locking arm 39, remote from the respective first end 39*a,* locates in an adjacent recess 45. As the locking arms 39 are prevented from rotating by the deflectable arms 43, the piston rod 24 is thereby prevented from moving under the force of the piston spring 25 by the locking arms 39.

A proximal end of the needle sleeve 23 includes contact portions 46 which are aligned with the lugs 44 of the deflectable arms 43 such that movement of the needle sleeve 23 longitudinally into the housing 21 brings the contact portions 46 into engagement with the respective adjacent lug 44. Advantageously, the contact portions 46 or the lugs 44, or both, may include a sloped surface. The surfaces of the contact portions 46 and the lugs 44 may further be sloped in the same direction so that the sloped faces come into substantial face contact when the contact portions 46 abut the lugs 44.

Operation of the injector device 20 of the first embodiment will now be described. The injector device 20 is initially configured with the release mechanism 26 in the starting locked position as shown in FIGS. 3 and 4. In this locked position, the piston rod 24 is prevented from movement under the force of the piston spring 25 as described above.

A user first removes the end cap 34 and then places the end of the needle sleeve 23 against the intended injection site on the patient's skin. The user then presses the injector device 20 towards the patient's skin which causes the needle sleeve 23 to move into the housing 21 from its extended position to its retracted position. As needle sleeve 23 retracts into the housing 21, the injection needle 32 is exposed and pierces the patient's skin in order for medicament to be delivered to the patient through the needle 32.

As the needle sleeve 23 retracts into the housing 21, contact portions 46 of the needle sleeve 23 engage the lugs 44 of the deflectable arms 43. Further movement of the needle sleeve 23 into the housing 21 causes the contact portions 46 to push the lugs 44 outwards and thereby deform the deflectable arms 43 outwards, as shown in FIG. 5. One or both of the surfaces of the contact portions 46 and the lugs 44 being sloped may advantageously help the deformation of the deflectable arms 43 as the needle sleeve 23 is moved to the retracted position. The deflectable arms 43 are thereby moved out of contact with the respective first ends 39*a* of the locking arms 39, and so the locking arms 39 are no longer prevented from rotating into the release position. Therefore, the piston rod 24 is released and is free to move under the force of the piston spring 25 longitudinally within the housing 21. It will be appreciated from the different sectional views of FIGS. 3 and 4 that the contact portions 46 of the needle sleeve 23 and the lugs 44 of the deflectable arms 43 are aligned in an axial direction of the injector device 20, but are out of alignment with the locking arms 39. Also, the locking arms 39 are in axial alignment with a portion of the deflectable arms 43 such that rotation of the locking arms 39 from the locking position to the release position can be prevented as described above. Therefore, the locking arms 39 do not obstruct the movement of the needle sleeve 23 and the contact portions 46 of the needle sleeve 23 can move past the locking arms 39 as the needle sleeve 23 moves to the retracted position.

As the piston rod 24 moves under the force of the piston spring 25, it pushes against the piston 30 of the medicament cartridge 27. It can be seen from FIG. 2 that in an initial configuration, before use, the needle unit 22 and medicament cartridge 27 are disposed within the housing 21 such that the needle 32 is spaced from the pierceable seal 29. As described above, in one embodiment, initial movement of the needle sleeve 23 causes the needle 32 to pierce the pierceable seal 29 before an injection procedure commences. Alternatively, however, as the medicament cartridge 27 is initially sealed by the pieceable seal 29 and the piston 30, the piston 30 cannot be pushed into the cylindrical container 28 and so the piston rod 24 may push the whole medicament cartridge 27 towards the needle unit 22, which may be fixed within the housing 21, until the needle 32 engages and pierces the pierceable seal 29. The distal end of the medicament cartridge then abuts the needle unit 22 and so cannot move further in the distal direction of the injector device 20. Thereafter, the piston rod 24 pushes the piston 30 into the cylindrical container 28 to cause the medicament 31 to be delivered into the patient's skin through the needle 32.

In a yet further alternative embodiment envisaged within the scope of the present disclosure, it is intended that as needle sleeve 23 retracts into the housing 21, it engages the needle unit 22 so that the needle unit 22 moves in the proximal direction with the needle sleeve 23 such that the needle 32 engages and pierces the pierceable seal 29 of the cartridge 27. Activation of the release mechanism 26 as described above may occur as the needle unit 22 engages the medicament cartridge 27, or may occur by further movement of the needle sleeve 23 into the housing 21 after the needle unit 22 disengages from the needle sleeve 23. However, the needle 32 may not yet pierce the patient's skin through movement of the needle sleeve 23 into the housing. Once the release mechanism 26 is activated as described above, the piston rod 24 may move under the force of the piston spring 24, pushing against the piston 30 of the medicament cartridge 27 such that the whole medicament cartridge 27 with engaged needle unit 22 is moved in the distal direction such that the needle 32 pierces the patient's skin and then the piston rod 24 pushes the piston 30 into the cylindrical container 28 to cause the medicament 31 to be delivered into the patient's skin through the needle 32.

In a yet further alternative embodiment envisaged within the scope of the present disclosure, the medicament cartridge 27 may be fixedly secured within the housing 21. In such an embodiment, as needle sleeve 23 retracts into the housing 21, it engages the needle unit 22 so that the needle unit 22 moves in the proximal direction with the needle sleeve 23 such that the needle 32 engages and pierces the pierceable seal 29 of the cartridge 27. Further movement of the needle sleeve 23 into the housing 21 results in the needle unit 22 disengaging from the needle sleeve 23 such that the injection needle 32 is exposed and pierces the patient's skin in order for medicament to be delivered to the patient through the needle 32. Also as the needle sleeve 23 retracts into the housing, the release mechanism 26 is activated as described above. As the piston rod 24 moves under the force of the piston spring 25, it pushes against the piston 30 of the medicament cartridge 27 and pushes the piston 30 into the cylindrical container 28 to cause the medicament 31 to be delivered into the patient's skin through the needle 32.

Once the medicament delivery process is complete, the user moves the injector device away from the patient's skin and the needle 32 is withdrawn from the skin. The needle sleeve 23 then biased to move back into the extended position to surround and conceal the needle 32 to prevent the user accidentally injuring themselves on the needle 32. A locking mechanism (not shown) may be provided to lock the needle sleeve 23 in the extended position after use of the device.

Figure 6:
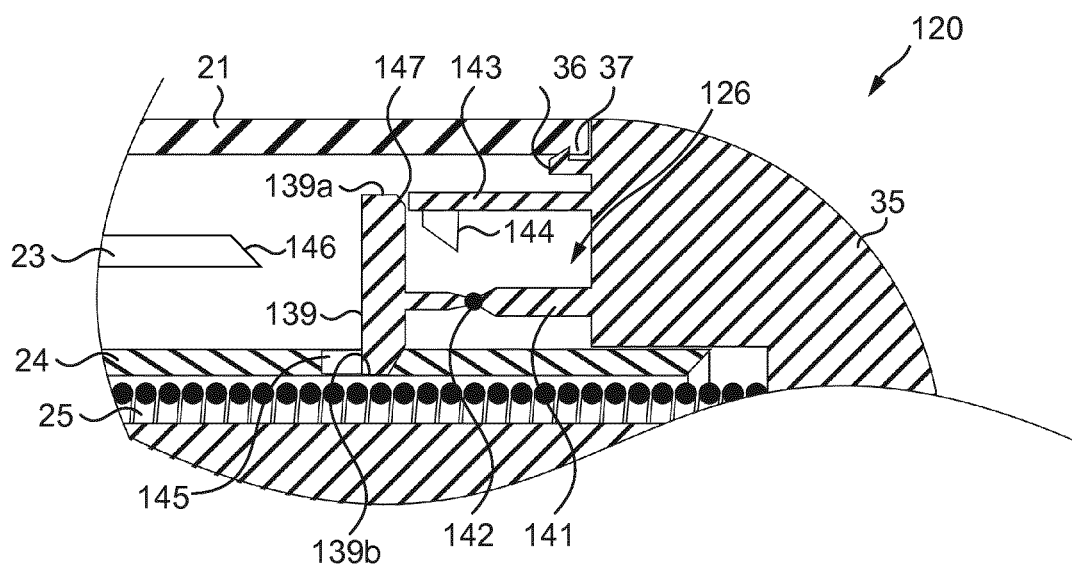
FIG. 6 is an enlarged cross-sectional view of a proximal end of an injector device of a second embodiment having an alternative configuration of release mechanism, shown in an initial, locked position.
Figure 7:
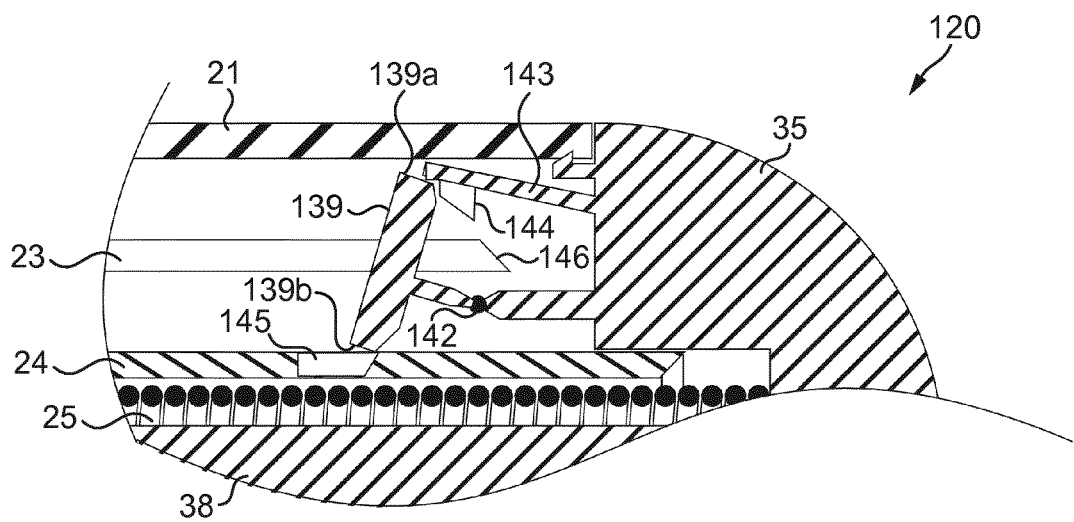
FIG. 7 is an enlarged cross-sectional view of the proximal end of the injector device of the second embodiment showing the release mechanism in an activated position.

FIGS. 6 and 7 show a release mechanism 126 of a second embodiment of injector device 120, and like features in common with the injector device 20 and release mechanism 26 of the first embodiment retain the same reference numerals, and detailed description thereof will not be repeated.

As with release mechanism 26 of the first embodiment, the release mechanism 126 of the second embodiment is configured to hold the piston rod 24 in a locked, starting position, against the force of the piston spring 25 and is configured to be actuated to a released or unlocked position to allow the piston rod 24 of move within the housing 21 under the force of the piston spring 25.

FIG. 6 shows the release mechanism 126 in the starting locked position, before a medicament delivery process is commenced and FIG. 7 shows the release mechanism 126 in the unlocked released position.

The release mechanism 126 of the second embodiment comprises a pair of locking arms 139 each mounted to a respective support post 141 at a pivot point 142 to enable the locking arms 139 to pivot between a locking position (shown in FIG. 6) and a release position (shown in FIG. 7). The locking arms 139 are substantially 'T'-shaped and comprise first and second ends 139a, 139b and are connected to the pivot point 142 intermediate the first and second ends 139a, 139b. The support posts 141 extend from the rear cap 35 and extend in a longitudinal direction of the housing 21, and are disposed on opposite sides, and on the outside, of the piston rod 24. Also extending from the rear cap 35 are deflectable arms 143 which are moveable from a relaxed state (shown in FIG. 6) to a deflected state (shown in FIG. 7). In the relaxed state, ends of the delectable arms 143 abut a respective first end 139a of the locking arms 139 when the locking arms 139 are in the locking position and thereby act as securing members and prevent the locking arms 139 from rotating into the release position. The deflectable arms 143 further comprise a respective inwardly-projecting lug 144.

The piston rod 24 includes a recess 145 on opposite sides thereof and disposed radially aligned with each locking arm 139. When the locking arms 139 are in the locking position, a respective second end 139b of each locking arm 139 locates in an adjacent recess 145 and the piston rod 24 is thereby prevented from moving under the force of the piston spring 25 by the locking arms 139.

As with the release mechanism 26 of the first embodiment, a proximal end of the needle sleeve 23 includes contact portions 146 which are aligned with the lugs 144 of the deflectable arms 143 such that movement of the needle sleeve 23 longitudinally into the housing 21 brings the contact portions 146 into engagement with the respective adjacent lug 144. Advantageously, the contact portions 146 or the lugs 144, or both, may include a sloped surface for the reasons and technical advantages described previously.

Operation of the injector device 120 of the second embodiment is similar to operation of the injector device 20 of the first embodiment, and only differences of the operation of the second embodiment will now be described. The injector device 120 is initially configured with the release mechanism 126 in the starting locked position as shown in FIG. 6 in which the piston rod 24 is prevented from movement under the force of the piston spring 25.

As the needle sleeve 23 retracts into the housing 21, contact portions 146 of the needle sleeve 23 engage the lugs 144 of the deflectable arms 143. Further movement of the needle sleeve 23 into the housing 21 causes the contact portions 146 to push the lugs 144 outwards and thereby deform the deflectable arms 143 outwards, as shown in FIG. 7, out of contact with the respective first ends 139a of the locking arms 139 so the locking arms 139 are no longer prevented from rotating into the release position. The piston rod 24 is thereby released and free to move under the force of the piston spring 25 longitudinally within the housing 21. As with the injector device 20 of the first embodiment, it will be appreciated that the contact portions 146 of the needle sleeve 23 and the lugs 144 of the deflectable arms 143 are aligned, but are out of alignment with the locking arms 39. Therefore, the locking arms 139 do not obstruct the movement of the needle sleeve 23 and the contact portions 146 of the needle sleeve 23 can move past the locking arms 139 as the needle sleeve 23 moves to the retracted position.

In this second embodiment of release mechanism 126, the contact portions 146 of the needle sleeve 23 and lug 144 of the deflectable arms 143 may be shaped so as to cause initial deformation of the deflectable arms 143 upon movement of the needle sleeve 23. The locking arm 139 may be shaped so that, thereafter, the force of the piston spring 25 pushing the piston rod 24 causes the deflectable arms 143 to be fully deformed out of engagement with the locking arms 139. For example, the first ends 139a of the locking arms 139 may include a sloped or chamfered edge 147 which may engaged the deflectable arms 143 to further deform the deflectable arms 143 out of engagement with the locking arms 139.

Thereafter, movement of the piston rod 24 and interaction with the medicament cartridge 27 to cause delivery of the medicament 31 to the patient, and subsequent withdrawal of the injector device 120, is as described previously with reference to the injector device 20 of the first embodiment.

In the second embodiment of release mechanism 126, the locking arms 139 and support posts 141 may comprise separate components connected together, or may be integrally formed components, and may also be integrally formed with the rear cap 35. In such an embodiment, the pivot point 142 may be a living hinge, thinner region of material, or other region of reduced material stiffness or strength, so that the locking arms 139 are able to pivot relative to the support posts 141 about the pivot points 142. In a yet further alternative variation of the second embodiment, the locking arms 139 and support posts 141 may be integrally formed such that the locking arms 139 comprise deflectable components that resiliently deform between the locking position and the release position, rather than pivoting about a pivot point. In such an embodiment, the locking arms may be in the locking position in a natural, undeflected state, and may be resiliently deformed into the release position. The locking arms 139 may have a smaller cross-sectional area along some or all of their length than the support posts 141, such that the majority of the deflection occurs at the locking arms 139 rather than at the support posts 141. That is, the pivot point 142 may be omitted and the locking arms may be thinner than the support posts 141 such that the deflection occurs at the locking arms 139.

Figure 8:
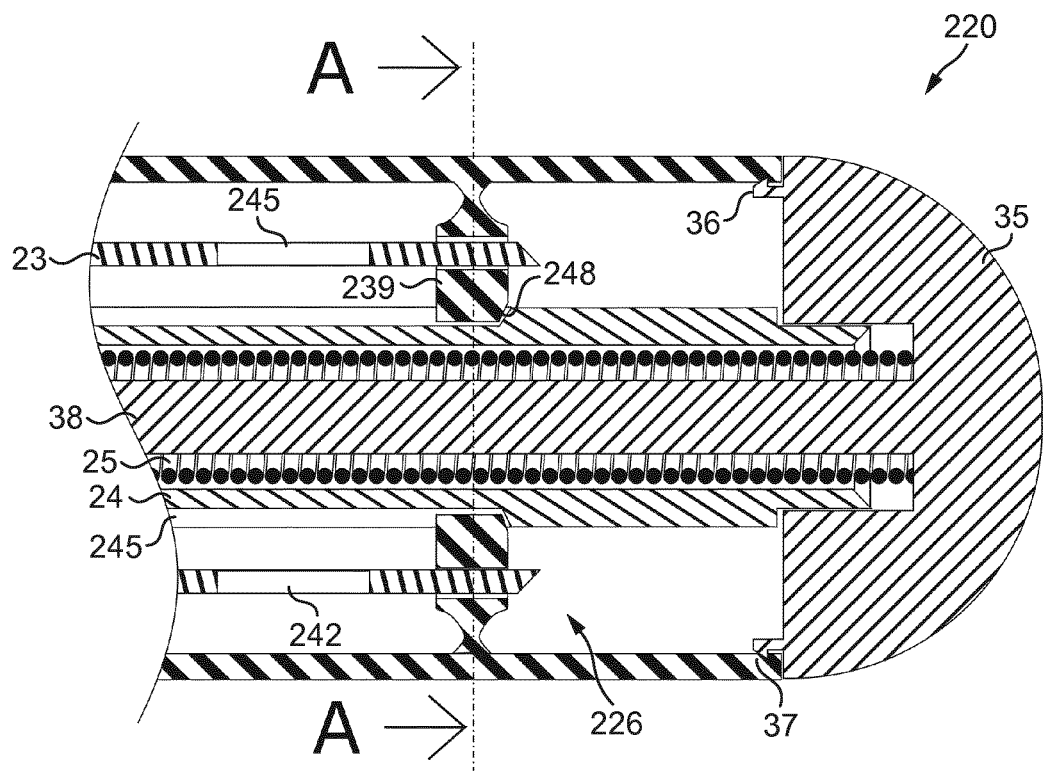
FIG. 8 is an enlarged cross-sectional view of a proximal end of an injector device of a third embodiment having an alternative configuration of release mechanism, shown in an initial, locked position.
Figure 9:
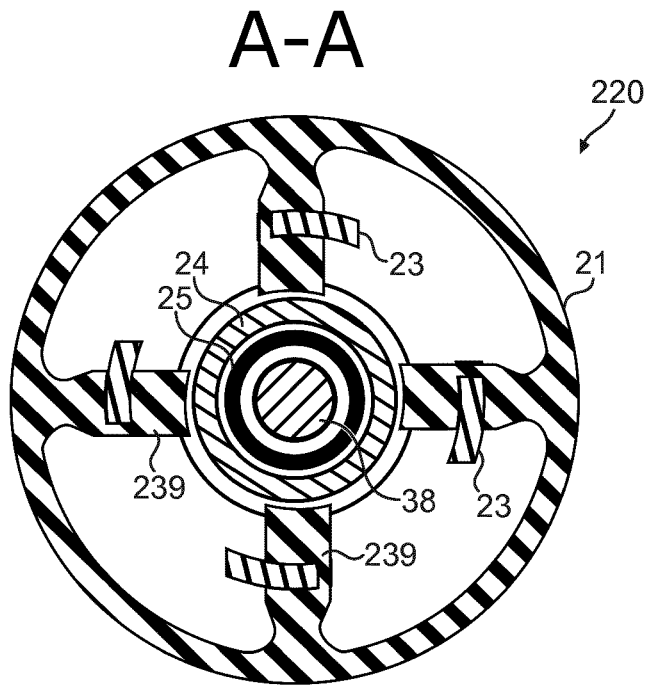
FIG. 9 is a cross-sectional view taken along the line A-A in FIG. 8 showing a rotatable release member of the release mechanism.
Figure 10:
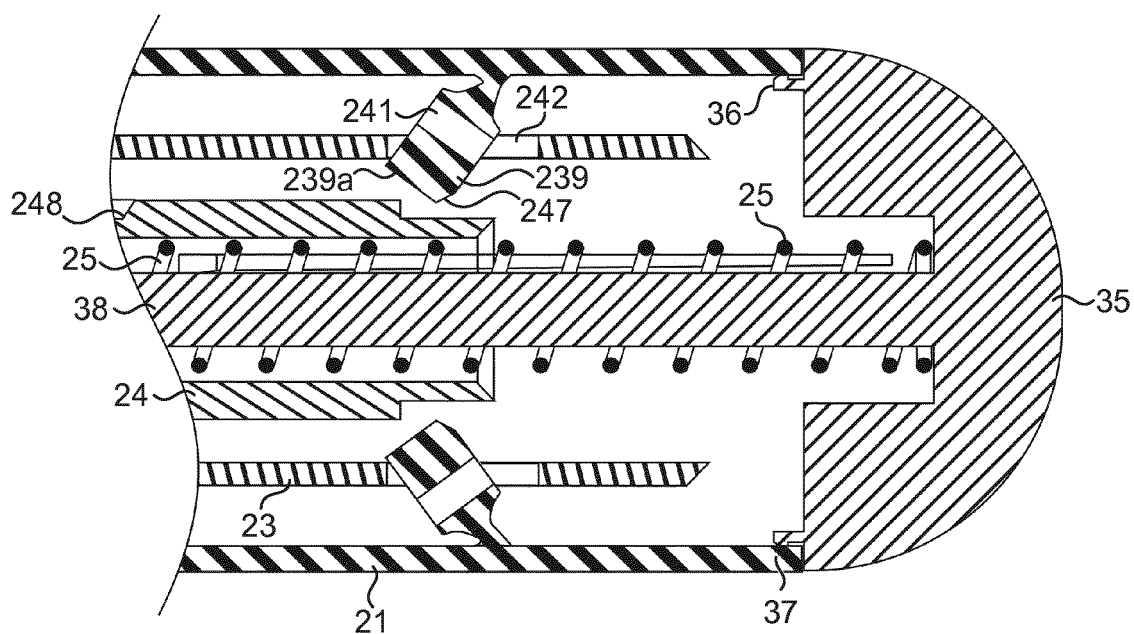
FIG. 10 is an enlarged cross-sectional view of the proximal end of the injector device of the third embodiment showing the release mechanism in an activated position.

FIGS. 8 to 10 show a release mechanism 226 of a third embodiment of injector device 220, and like features in common with the injector devices 20, 120 and release mechanisms 26, 126 of the first and second embodiments retain the same reference numerals, and detailed description thereof will not be repeated.

As with release mechanisms 26, 126 of the first and second embodiments, the release mechanism 226 of the third embodiment is configured to hold the piston rod 24 in a locked, starting position, against the force of the piston spring 25 and is configured to be actuated to a released or unlocked position to allow the piston rod 24 of move within the housing 21 under the force of the piston spring 25.

FIG. 8 shows the release mechanism 226 in the starting locked position, before a medicament delivery process is commenced and FIG. 10 shows the release mechanism 226 in the unlocked released position. FIG. 9 shows a cross-section through the housing 21 along the line A-A shown in FIG. 8.

The release mechanism 226 of the third embodiment comprises a plurality of locking arms 239 which are configured to engage the piston rod 24 to hold it in the locked starting position. However, unlike the first and second embodiment, the locking arms 239 are provided on the housing 21 rather than the rear cap 35. The locking arms 239 may be bonded to, or formed integrally with, the housing 21, and extend inwardly from an inside surface of the housing 21, as can be seen in FIGS. 8 to 10. The locking arms 239 are moveable between a locking position (shown in FIGS. 8 and 9) and a release position (shown in FIG. 10).

The piston rod 24 includes recesses 245 into which an end 239a of each locking arm 239 is located when the locking arms 239 are in the locking position and the piston rod 24 is in the locked starting position, as shown in FIG. 8. When the locking arms 239 are in the locking position, the ends 239a of the locking arms 239 located in the recesses 245 prevent the piston rod 24 from moving under the force of the piston spring 25.

Each locking arm 239 also includes a slot 241. A portion of the needle sleeve 23 which acts as a securing member is received within the slot 241 when the needle sleeve 23 is in the extended position, as shown in FIGS. 8 and 9. The needle sleeve 23 being received in the slots 241 prevents the locking arms 239 from being deflected by the piston rod 24 under the force of the piston spring 25.

The needle sleeve 23 also includes apertures 242 at a point that is aligned with the locking arms 239 when the needle sleeve is in the retracted position.

Operation of the injector device 220 of the third embodiment is similar to operation of the injector devices 20, 120 of the first and second embodiments, and only differences of the operation of the third embodiment will now be described. The injector device 220 is initially configured with the release mechanism 226 in the starting locked position as shown in FIGS. 8 and 9, in which the piston rod 24 is prevented from movement under the force of the piston spring 25.

As the needle sleeve 23 retracts into the housing 21, the apertures 242 in the needle sleeve 23 come into alignment with the slots 241 in the locking arms 239. At this point, the needle sleeve 23 no longer holds the locking arms 239 in the locking position and the locking arms 239 are free to be deflected. Thereafter, the force of the piston spring pushes the piston rod 24 and deflects the locking arms 239 into the release position so that the ends 239a of the locking arms 239 are no longer received within the recesses 245 of the piston rod 24. The piston rod 24 is thereby released and free to move under the force of the piston spring 25 longitudinally within the housing 21. Thereafter, movement of the piston rod 24 and interaction with the medicament cartridge 27 to cause delivery of the medicament 31 to the patient, and subsequent withdrawal of the injector device 220, is as described previously with reference to the injector device 20 of the first embodiment.

In this third embodiment of release mechanism 226, the locking arms 239 and the recesses 245 in the piston rod 24 may be shaped to encourage deflection of the locking arms 239 once released by movement of the needle sleeve 23. For example, the ends 239a of the locking arms 239 may include a sloped or chamfered edge 247. Similarly, an end 248 of the recesses 245 which abuts the locking arms 239 in the locking position may alternatively, or also, include a chamfered edge.

Variations of the third embodiment 226 of release mechanism are envisaged. Such variations may comprise a separate retaining pin that retains the locking arms 239 in the locking position and so holds the piston rod 24 in the starting locked position. The needle sleeve 23 may comprise a portion that engages and releases the retaining pins once the needle sleeve 23 is in the retracted position to release the piston rod 24. In a further variation, the needle sleeve 23 may be formed in two parts, a distal part and a proximal part. The distal and proximal needle sleeve parts may initially be in contact and in the position shown in FIG. 8. The proximal part of the needle sleeve 23 would include the portion that is received within the slots 241 of the locking arms 239, and the apertures 242 in the needle sleeve 23. In use, movement of the needle sleeve 23 into the retracted position would comprise the distal part being pressed against a patient's skin and moving into the housing 21, and the distal part of the needle sleeve 23 then pushing the proximal part into the housing 21. Once the proximal part of the needle sleeve 23 is pushed into the retracted position, the apertures 242 in the needle sleeve 23 come into alignment with the slots 241 in the locking arms 239 so that the needle sleeve 23 no longer holds the locking arms 239 in the locking position, as described above. Thereafter, once the medicament delivery process is complete and the injector device 220 is withdrawn from the patient's skin, the proximal part of the needle sleeve may remain in the retracted position, and a needle sleeve spring (not shown) may bias only the distal part of the needle sleeve 23 back into the extended position to enclose the needle 32. The may advantageously avoid possible catching of the needle sleeve 23 on the slots 242 of the locking arms 239 as the needle sleeve 23 returns to the extended position.

Figure 11:
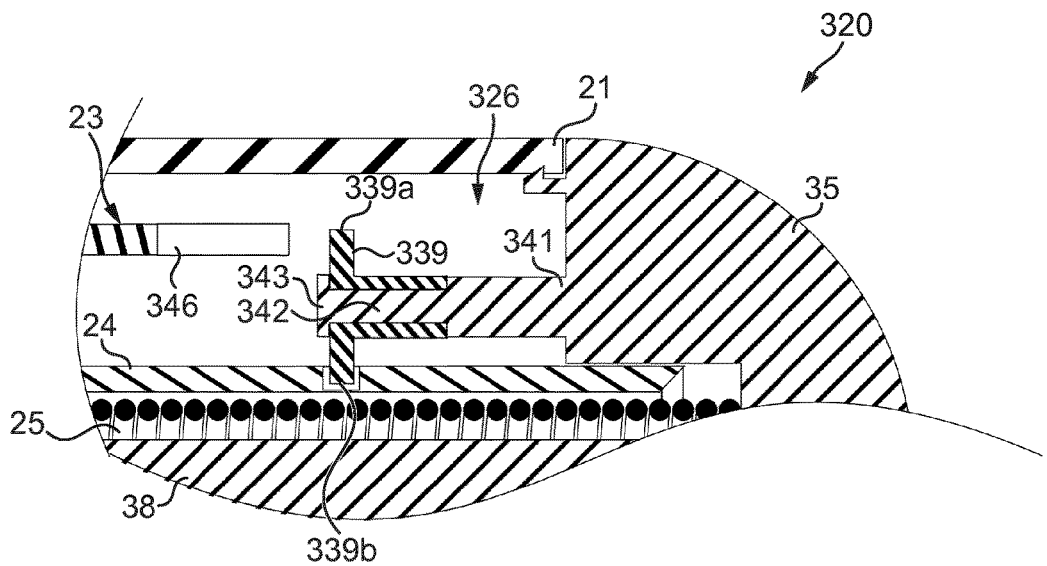
FIG. 11 is an enlarged cross-sectional view of a proximal end of an injector device of a fourth embodiment having an alternative configuration of release mechanism, shown in an initial, locked position.
Figure 12:
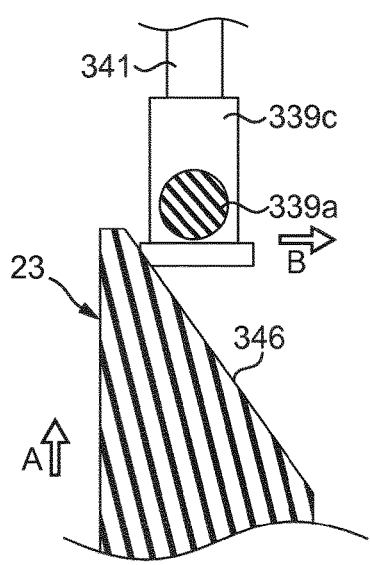
FIG. 12 is a schematic plan view of a portion of the release mechanism of the injector device of the fourth embodiment shown in FIG. 11 in the initial, locked position.
Figure 13:
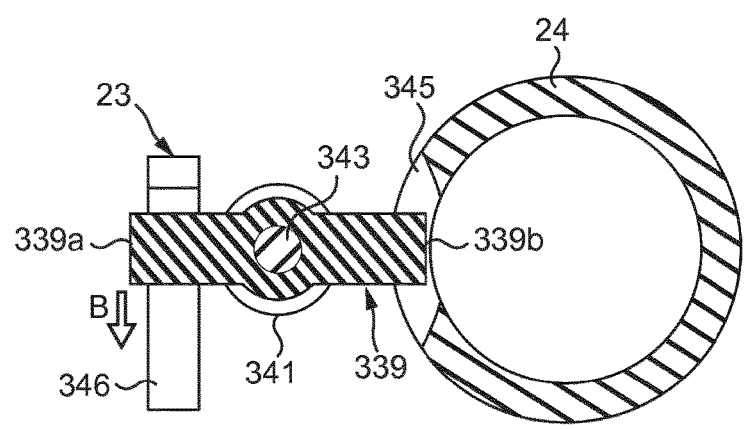
FIG. 13 is a schematic end view of a portion of the release mechanism and piston rod of the injector device of the fourth embodiment shown in FIG. 11 in the initial, locked position.

FIGS. 11 to 13 show a release mechanism 326 of a fourth embodiment of injector device 320, and like features in common with the injector devices 20, 120, 220 and release mechanisms 26, 126, 226 of the first, second and third embodiments retain the same reference numerals, and detailed description thereof will not be repeated.

The release mechanism 326 of the fourth embodiment is configured to hold the piston rod 24 in a locked, starting position, against the force of the piston spring 25 and is configured to be actuated to a released or unlocked position to allow the piston rod 24 of move within the housing 21 under the force of the piston spring 25.

FIG. 11 shows the release mechanism 326 in the starting locked position, before a medicament delivery process is commenced. FIG. 12 shows a schematic plan view of a portion of the release mechanism 326 in the starting locked position, and FIG. 13 shows a schematic end view of a portion of the release mechanism 326 and piston rod 24 in the starting locked position.

The release mechanism 326 of the fourth embodiment comprises a pair of locking arms 339 each mounted to a respective support post 341 at a pivot point 342 to enable the locking arms 339 to pivot between a locking position (shown in FIGS. 11 and 13) and a release position (not shown). The locking arms 339 comprise first and second ends 339a, 339b and are connected to the pivot point 342 intermediate the first and second ends 339a, 339b. Each pivot point 342 comprises a pin extending coaxial with the support post 341, and the locking arms 339 are connected to the respective pivot point 342 by a tubular portion 339c of the locking arm 339 which is disposed over, and coaxial with, the pin of the respective pivot point 342. Each locking arm 339 is thereby rotatable about an axis of the pin of the respective pivot point 342. Each pin includes an enlarged head 343 that prevents the locking arm 339 from sliding off the pin, but allows the locking arm 339 to rotate relative to the pin.

The support posts 341 extend from the rear cap 35 and extend in a longitudinal direction of the housing 21, and are disposed on opposite sides, and on the outside, of the piston rod 24.

The piston rod 24 includes a recess 345 on opposite sides thereof and disposed radially aligned with each locking arm 339. When the locking arms 339 are in the locking position, a respective second end 339b of each locking arm 339 locates in an adjacent recess 345 (see FIG. 13) and the piston rod 24 is thereby prevented from moving under the force of the piston spring 25 by the locking arms 339.

A proximal end of the needle sleeve 23 includes contact portions 346 which are aligned with the first ends 339a of the locking arms 339 in a longitudinal direction of the injector device 320, when the locking arms 339 are in the starting locking position. The contact portions 346 of the needle sleeve 23 may be spaced from, or in contact with, the first ends 339a of the locking arms when the needle sleeve 23 is in the extended position and the locking arms 339 are in the starting locking position.

The contact portions 346 of the needle sleeve 23 are configured such that as the needle sleeve 23 is moved longitudinally into the housing 21 into the retracted position, the contact portions 346 engage the respective first ends 339a of the locking arms and urge the locking arms 339 to pivot about the pivot point 342. Such configuration of contact portion 346 may comprise an angled face, as can be seen in FIGS. 12 and 13, such that as the needle sleeve 23 moves to the retracted position in the direction of arrow 'A' in FIG. 12, the first end 339a of the locking arm 339 is urged in the direction of arrow 'B' in FIGS. 12 and 13.

Operation of the injector device 320 of the fourth embodiment is similar to operation of the injector devices 20, 120, 220 of the first, second and third embodiments, and only differences of the operation of the fourth embodiment will now be described. The injector device 320 is initially configured with the release mechanism 326 in the starting locked position as shown in FIGS. 11 and 13, in which the piston rod 24 is prevented from movement under the force of the piston spring 25.

As the needle sleeve 23 retracts into the housing 21, contact portions 346 of the needle sleeve 23 engage the respective first ends 339a of the locking arms 339. Further movement of the needle sleeve 23 into the housing 21 causes the contact portions 346 to push the first ends 339a of the locking arms 339 in the direction of arrows 'B' in FIGS. 12 and 13 and so the locking arms 339 rotate about the axis of the pin of the respective pivot point 342. This causes the respective second end 339b of each locking arm 339 to rotate out of the respective recess 345 in the piston rod 24. The piston rod 24 is thereby released and free to move under the force of the piston spring 25 longitudinally within the housing 21. Thereafter, movement of the piston rod 24 and interaction with the medicament cartridge 27 to cause delivery of the medicament 31 to the patient, and subsequent withdrawal of the injector device 320, is as described previously with reference to the injector device 20 of the first embodiment.

Although in the fourth embodiment of release mechanism 326 described above, the needle sleeve comprises a sloped contact face 346 which engages with the locking arm 339, alternative suitable cooperating configurations of needle sleeve 23 and locking arms 339 are envisaged. Such alternative configurations would also result in pivoting of the locking arms through movement of the needle sleeve 23 to the retracted position. For example, the first end 339a of the locking arms 339 may be received in a shaped slot or track within the needle sleeve 23 which guides the locking arms 339 to rotate as the needle sleeve 23 is retracted into the housing 21.

Figure 14:
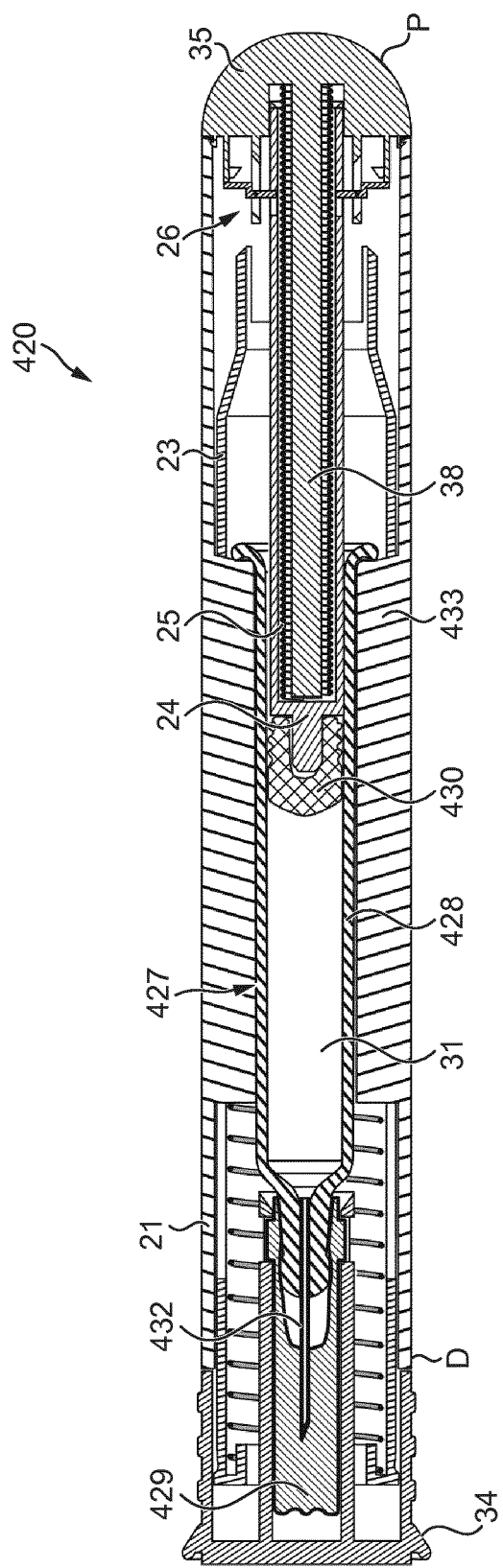
FIG. 14 is a cross-sectional side view of an injector device of a fifth embodiment.

FIG. 14 shows an injector device 420 of a fifth embodiment in which features in common with the injector device 20 of the first embodiment retain the same reference numerals and detailed description thereof will not be repeated. The injector device 420 of the fifth embodiment comprises a housing 21, a needle sleeve 23, a piston rod 24, a piston spring 25, and a release mechanism 26 as described previously with respect to the injector device 20 of the first embodiment.

A difference with the injector device 420 of the fifth embodiment is that the housing 21 is configured to contain a different type of medicament container, namely a pre-filled syringe 427 instead of a medicament cartridge 27 as in the first embodiment. The pre-filled syringe 427 comprises a cylindrical body 428 having a distal end which a needle 432 is fixed, and a proximal end which is sealed with a piston 430 disposed within the proximal end of the cylindrical body 428. Medicament 31 is held within the cylindrical body 428 between the needle 432 and the piston 430. The pre-filled syringe 427 is fixedly retained within the housing 21. In the exemplary embodiment shown, the pre-filled syringe is held in a syringe holder 433 within the housing 21. Such syringe holder 427 may be formed integrally with the housing 21, as shown in FIG. 14, or may be a separate component secured within the housing 21.

A needle cap 429 is provided around the needle 432 and is in frictional engagement with a narrowed portion of the cylindrical body 428 at its distal end that retains the needle 432. The needle cap 429 is received within the end cap 34 and is secured to the end cap 34 such that removal of the end cap 34 causes the needle cap 429 to be separated from the cylindrical body 428. The needle cap 429 may be secured to the end cap 34 by frictional engagement or by bonding, or by being otherwise mechanically secured to the end cap 34.

As with the medicament delivery device 20 of the first embodiment, the needle sleeve 23 is configured to slide within the housing 21 between an extended position in which the needle sleeve 23 surrounds the needle 432 and a retracted position in which the needle 432 is exposed beyond the end of the needle sleeve 23. The needle sleeve 23 is shown in the extended position in FIG. 14.

The release mechanism 26 is as described previously with respect to the injector device 20 of the first embodiment and so will not be described again.

Operation of the injector device 420 of the fifth embodiment will now be described. The injector device 420 is initially in the starting position in which the release mechanism 26 is configured as shown in FIG. 14.

A user first removes the end cap 34 and with it the needle cap 429, and then places the end of the needle sleeve 23 against the intended injection site on the patient's skin. The user then presses the injector device 420 towards the patient's skin which causes the needle sleeve 23 to move into the housing 21 from its extended position to its retracted position. As needle sleeve 23 retracts into the housing 21, the needle 432 is exposed and pierces the patient's skin.

As the needle sleeve 23 retracts into the housing 21, contact portions 46 of the needle sleeve 23 engage the lugs 44 of the deflectable arms 43. Further movement of the needle sleeve 23 into the housing 21 causes the contact portions 46 to push the lugs 44 outwards and thereby deform the deflectable arms 43 outwards, as shown in FIG. 5. The deflectable arms 43 are thereby moved out of contact with the respective first ends 39a of the locking arms 39, and so the locking arms 39 are no longer prevented from rotating into the release position. Therefore, the piston rod 24 is released and is free to move under the force of the piston spring 25 longitudinally within the housing 21.

As the piston rod 24 moves under the force of the piston spring 24, it pushes against the piston 430 of the pre-filled syringe 427. Since the pre-filled syringe 427 is fixedly held within the housing 21, the piston rod 24 pushes the piston 430 into the cylindrical body 428 of the pre-filled syringe 427 to cause the medicament 31 to be delivered into the patient's skin through the needle 132.

Once the medicament delivery process is complete, the user moves the injector device 420 away from the patient's skin and the needle 432 is withdrawn from the skin. The needle sleeve 23 then moves back into the extended position to surround and conceal the needle 432 to prevent the user accidentally injuring themselves on the needle 432. A locking mechanism (not shown) may be provided to lock the needle sleeve 23 in the extended position after use of the device.

FIGS. 15 to 19 show an injector device 520 according to a sixth embodiment of the invention. The injector device 520 of the sixth embodiment comprises a distal end D and a proximal end P and includes a release mechanism 526 similar to that of the first embodiment, and like features retain the same reference numerals. A difference with the sixth embodiment is that a rear cap 535 is moveable relative to the housing 21 and a number of components of the release mechanism 526 are secured to and moveable with the rear cap 535 to activate the release mechanism 526, as will be described hereafter. Also, as with the injector device 420 of the fifth embodiment, the injector device 520 of the sixth embodiment is configured to receive a pre-filled syringe 527 of medicament.

The injector device 520 of the sixth embodiment comprises a housing 21, a piston rod 24, a piston spring 25, and a release mechanism 526. The housing 21 is configured to contain a pre-filled syringe 527 comprising a cylindrical body 528 having a distal end in which a needle 532 is fixed, and a proximal end which is sealed with a piston 530 disposed within the proximal end of the cylindrical body 528. Medicament 31 is held within the cylindrical body 528 between the needle 532 and the piston 530. The pre-filled syringe 527 is retained within the housing 21 in a syringe holder 533. The syringe holder 533 is moveable between a retracted position (shown in FIGS. 15, 17 and 19) and an extended position (shown in FIG. 18). In the retracted position, the needle 532 is fully received within the housing 21, and in the extended position, the needle 532 extends out of the distal end of the housing 21 and is exposed to enable insertion into the skin of a patient.

The syringe holder 533 comprises first projections 548 which engage with cooperating first stops 549 which project inwardly from the inside wall of the housing 21 to prevent movement of the syringe holder 533 further into the housing in the proximal direction beyond the retracted position. The syringe holder 533 comprises second projections 550 which engage with cooperating second stops 551 which project inwardly from the inside wall of the housing 21 to prevent movement of the syringe holder 533 further out of the housing 21 in the distal direction beyond the extended position.

The release mechanism 526 is configured to retain the piston rod 24 in an initial primed and locked position against the force of the piston spring 25, and upon activation, to release the piston rod 24 to be able to move under the force of the piston spring 25, as described in hereafter.

Figure 15:
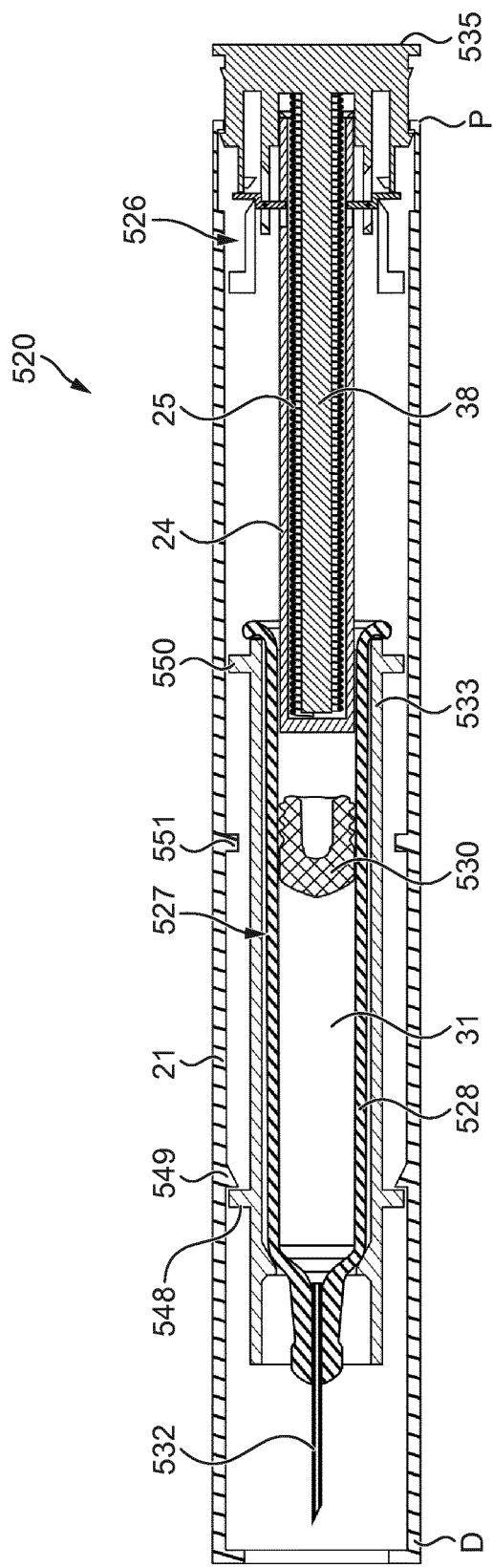
FIG. 15 is a cross-sectional side view of an injector device of a sixth embodiment.
Figure 16:
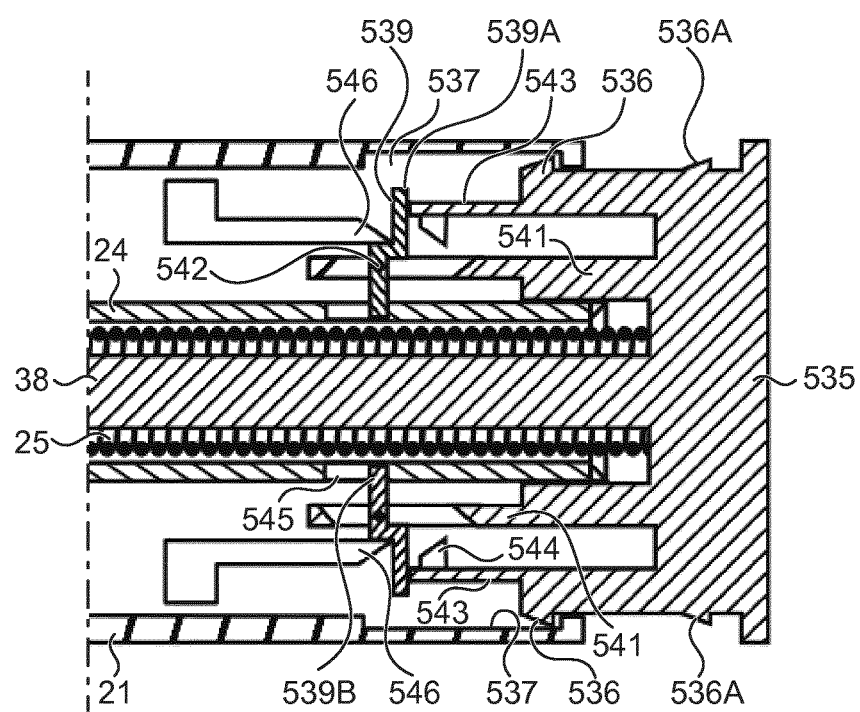
FIG. 16 is an enlarged cross-sectional view of a proximal end of the injector device of the sixth embodiment shown in FIG. 15 with a release mechanism shown in an initial, locked position.

The rear cap 535 is provided at the proximal end of the injector device 520 and is retained in place by retaining arms 536 which engage with corresponding retaining portions 537 formed on the housing 21 (see FIG. 16). The retaining portions 537 formed on the housing 21 comprise recessed slots within which the retaining arms 536 can slide to allow the rear cap 535 to move between a first, extended position (shown in FIGS. 15 and 16) and a second, depressed position (shown in FIGS. 17, 18 and 19). The rear cap 535 also includes latch portions 536A which can engage with the end of the recessed slots of the retaining portions 537 to retain the rear cap 535 in the depressed position once the rear cap 535 is moved into the depressed position.

The piston spring 25 is disposed around an elongate projection 38 extending from the rear cap 535. The piston rod 24 has a hollow bore and is disposed over the elongate projection 38 and piston spring 25 such that the elongate projection 38 and piston spring 25 are received within the hollow bore of the piston rod 24. The piston spring 25 is in contact with the rear cap 535 and is configured to urge the piston rod 24 in a distal direction of the injector device 520. When a pre-filled syringe 527 is received within the injector device 520, the piston rod 24 is initially space from the piston 530 (see FIG. 15) but is configured to drive the piston 530 within the cylindrical container 528 once the piston rod 24 is released.

The piston rod 24 is initially held in locked, starting position (shown in FIG. 15), against the force of the piston spring 25 by the release mechanism 526. The release mechanism 526 is configured to be actuated to a released or unlocked position, to allow the piston rod 24 of move within the housing 21 under the force of the piston spring 25, as described in more detail below.

The release mechanism 526 of the sixth embodiment can be seen in more detail in FIG. 16 which shows the release mechanism 526 in the starting locked position, before a medicament delivery process is commenced.

Figure 17:
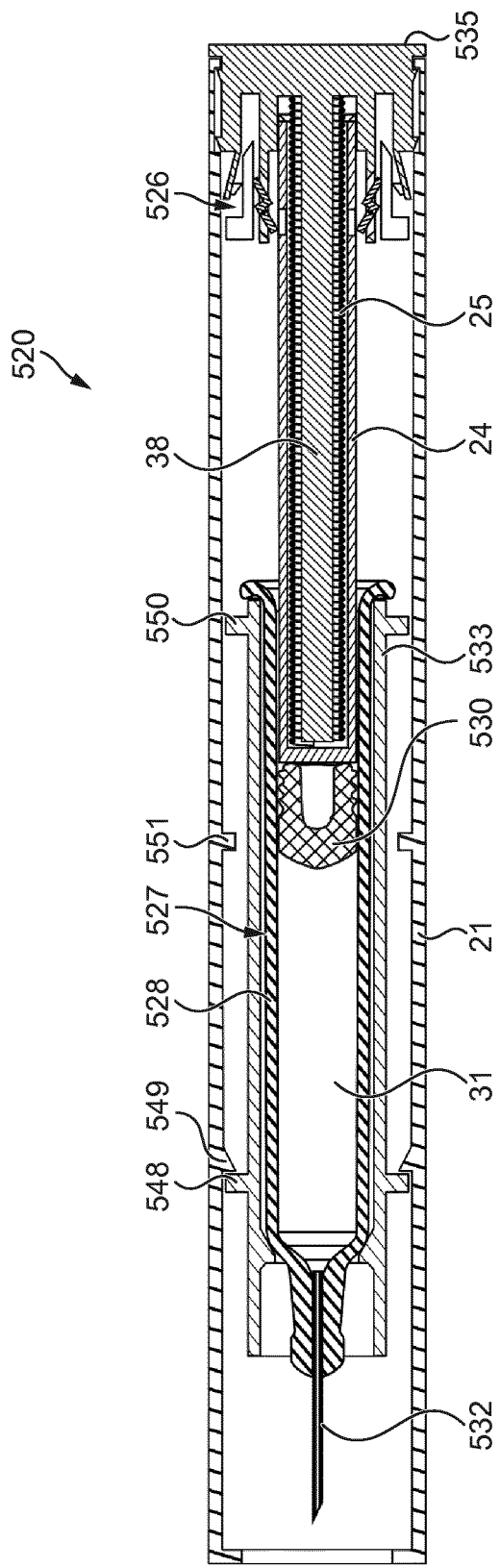
FIG. 17 is a cross-sectional side view of the injector device of the sixth embodiment shown in FIG. 15 showing the release mechanism in an activated position.
Figure 18:
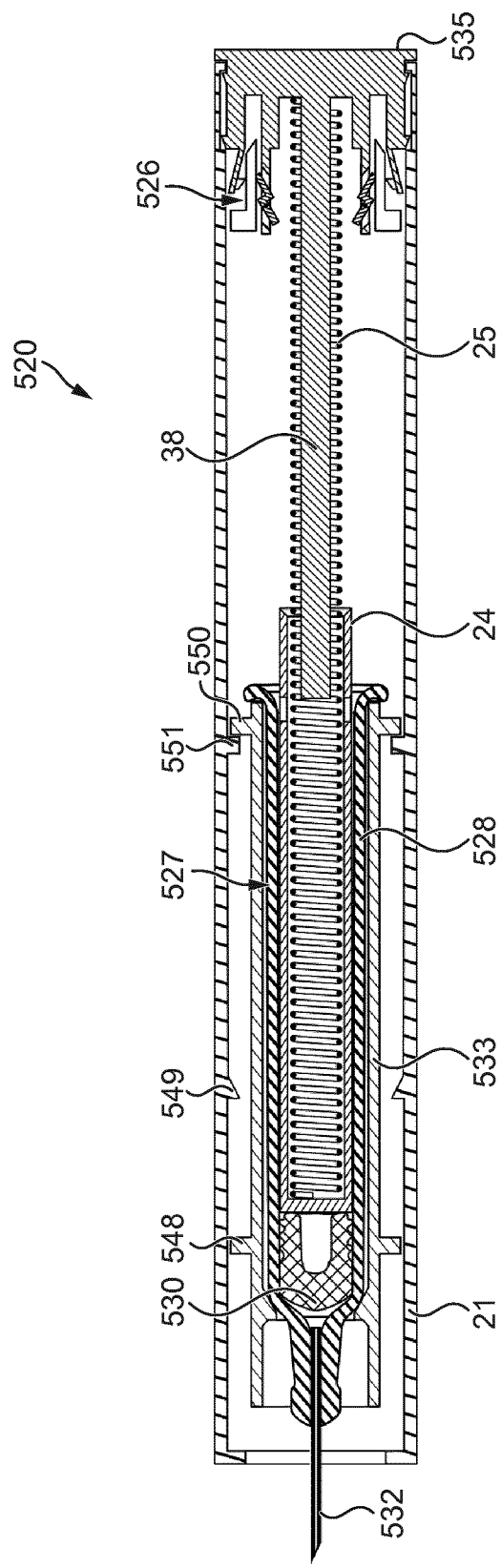
FIG. 18 is a cross-sectional side view of the injector device of the sixth embodiment shown in FIG. 15 showing the release mechanism in an activated position and with the piston rod having pushed the piston fully into the medicament container to expel the medicament.
Figure 19:
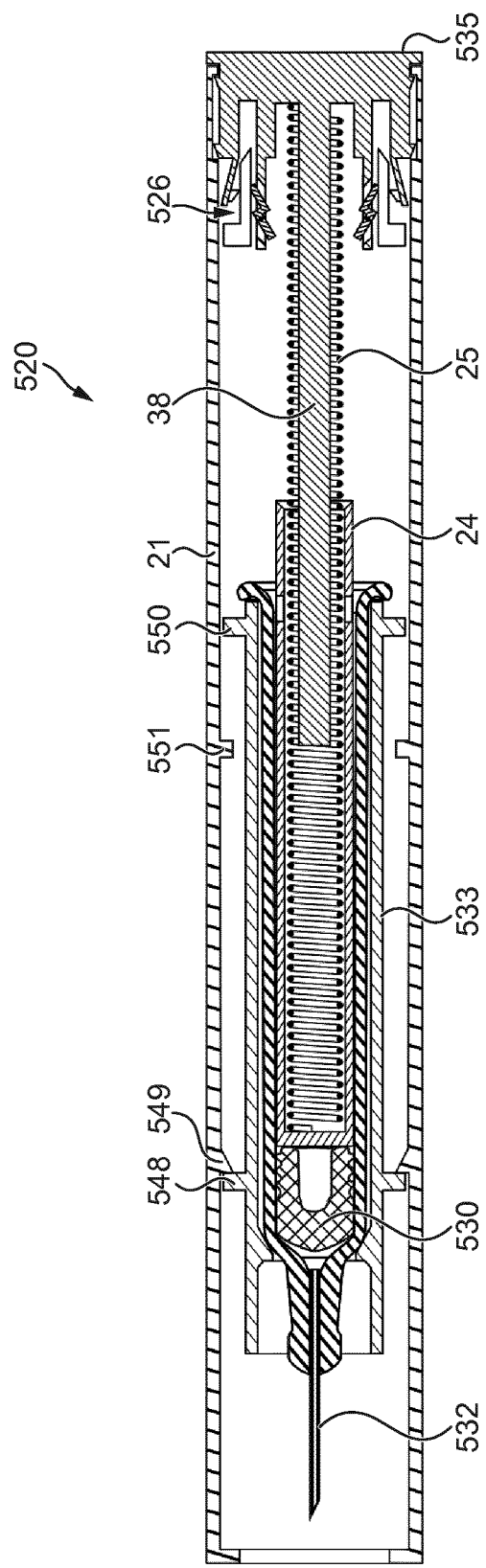
FIG. 19 is a cross-sectional side view of the injector device of the sixth embodiment shown in FIG. 15 showing the release mechanism in an activated position, after the piston rod has pushed the piston fully into the medicament container to expel the medicament, and with the release mechanism and needle retracted into the housing of the injector device.

The release mechanism 526 comprises a pair of locking arms 539 each mounted to a respective support post 541 at a pivot point 542 to enable the locking arms 539 to pivot between a locking position (shown in FIGS. 15 and 16) and a release position (shown in FIGS. 17, 18 and 19). The support posts 541 extend from the rear cap 535 and extend in a longitudinal direction of the housing 21, and are disposed on opposite sides, and on the outside, of the piston rod 24. Also extending from the rear cap 535 are deflectable arms 543. The deflectable arms 543 are moveable from a relaxed state (shown in FIGS. 15 and 16) to a deflected state (shown in FIGS. 17, 18 and 19). In the relaxed state, ends of the delectable arms 543 abut a respective first end 539a of the locking arms 539 when the locking arms 539 are in the locking position. The deflectable arms 543 in the relaxed state thereby act as securing members and prevent the locking arms 539 from pivoting into the release position. The deflectable arms 543 further comprise a respective inwardly-projecting lug 544.

The piston rod 24 includes a recess 545 on opposite sides thereof and disposed radially aligned with each locking arm 539. When the locking arms 539 are in the locking position, a respective second end 539b of each locking arm 539, remote from the respective first end 539a, locates in an adjacent recess 545. As the locking arms 539 are prevented from rotating by the deflectable arms 543, the piston rod 24 is thereby prevented from moving under the force of the piston spring 25 by the locking arms 539.

The inside of the housing 21 includes contact portions 546 which are fixed relative to the housing 21 and aligned with the lugs 544 of the deflectable arms 543. Movement of the rear cap 535 longitudinally into the housing 21 from the extended position to the depressed position brings the contact portions 546 into engagement with the respective adjacent lug 544. Advantageously, the contact portions 546 or the lugs 544, or both, may include a sloped surface. The surfaces of the contact portions 546 and the lugs 544 may further be sloped in the same direction so that the sloped faces come into substantial face contact when the contact portions 546 abut the lugs 544.

Operation of the injector device 520 of the sixth embodiment will now be described. The injector device 520 is initially configured with the release mechanism 526 in the starting locked position as shown in FIGS. 15 and 16. In this locked position, the piston rod 24 is prevented from movement under the force of the piston spring 25 as described above.

A user places the distal end D of the housing 21 against the intended injection site on their or the patient's skin. The user then presses the rear cap 535 inwards in the distal direction of the injector device 520 from the extended position into the depressed position. The latch portions 536A engage with the end of the recessed slots of the retaining portions 537 to retain the rear cap 535 in the depressed position. As the rear cap 535 moves to the depressed position, contact portions 546 engage the lugs 544 of the deflectable arms 543. Further movement of the rear cap 535 into the depressed position causes the contact portions 546 to push the lugs 544 outwards and thereby deform the deflectable arms 543 outwards, as shown in FIGS. 17, 18 and 19. One or both of the surfaces of the contact portions 546 and the lugs 544 being sloped may advantageously help the deformation of the deflectable arms 543 as the rear cap 535 is moved to the depressed position. The deflectable arms 543 are thereby moved out of contact with the respective first ends 539a of the locking arms 539, and so the locking arms 539 are no longer prevented from rotating into the release position. Therefore, the piston rod 24 is released and is free to move under the force of the piston spring 25 longitudinally within the housing 21. It will be appreciated that in the exemplary sixth embodiment shown in FIGS. 15 to 19, the rear cap 535 comprises an actuator configured to operate the release mechanism 526.

It will be appreciated that, as with the release mechanism 26 of the first embodiment, the contact portions 546 of the housing 21 and the lugs 544 of the deflectable arms 543 are aligned in an axial direction of the injector device 520, but are out of alignment with the locking arms 539. Also, the locking arms 539 are in axial alignment with a portion of the deflectable arms 543 such that rotation of the locking arms 539 from the locking position to the release position can be prevented as described above. Therefore, the locking arms 539 do not obstruct the movement of the rear cap 535 and the locking arms 539 can move past the contact portions 546 of the housing 21 as the rear cap 535 moves to the depressed position.

As the piston rod 24 moves under the force of the piston spring 25, it first comes into contact with the piston 530 (see FIG. 18), and then pushes against the piston 530. The free movement of the syringe holder 533 within the housing 21, and the viscosity of the medicament 31, together with bore of the needle 532 and the force required to expel the medicament 31 out of the cylindrical container 538 through the needle 532, is such that the piston rod 24 initially pushes whole syringe holder 533 together with the syringe 527, towards the distal end of the housing 21. The distal end of the needle 532 extends out of the distal end of the housing 21 (see FIG. 18) and pierces the patient's skin. The movement of the syringe holder 533 in the distal direction is stopped when the second projections 550 abut the second stops 551. Thereafter, the piston rod 24 pushes the piston 530 into the cylindrical container 528 to cause the medicament 31 to be delivered into the patient's skin through the needle 532.

Once the medicament delivery process is complete, the user moves the injector device 520 away from the patient's skin and the needle 532 is withdrawn from the skin by a syringe retraction mechanism (not shown). The syringe holder 533 moves back into the retracted position until the first projections 548 abut the first stops 549 so that the needle 532 is concealed within the housing 21 (see FIG. 19) to prevent the user accidentally injuring themselves on the needle 532. A locking mechanism (not shown) may be provided to lock the syringe holder 533 in the retracted position after use of the device.

Although in the embodiments described above, a particular number of locking arms 39, 139, 239, 339, 539 and corresponding recesses 45, 145, 245, 345, 545 in the piston rod 24 are described in each embodiment, it is intended within the scope of the invention that different numbers of such features may be provided. Although in the embodiments described above, the piston rod is described as comprising one or more recesses 45, 145, 245, 345, 545 within which an end of a respective locking arm is received in the locking position, it will be appreciated that alternative configurations of release mechanism are intended within the scope of the invention, and instead of recesses formed in the piston rod, the piston rod may alternatively comprise one or more projections, ledge or other abutment, for example projecting in a generally radial direction outwards from the outer surface of the piston rod. Such projections may provide an abutment surface against which an end of a respective locking arm abuts in a locking position to hold the piston rod in the initial primed and locked starting position. In such alternative embodiments, each locking arm would be slightly shorter than in the illustrated embodiments as the end of the locking arm would not need to extend into any recess in the piston rod in the locking position, and instead only need to extend sufficiently close to the outer surface of the piston rod to be in abutment with the projection.

It will be appreciated that in the various embodiments described above, the locking arms are generally moveable between the locked and release positions, and are so moveable in a number of ways within the various embodiments described, for example by pivoting, flexing, resiliently deflecting, and rotating.

A number of different release mechanisms are envisaged with the various embodiments described above and as illustrated. The release mechanism of the sixth embodiment shown in FIGS. 15-19 which is actuated by movement of the rear cap from the extended position to the depressed position shares a number of features in common with the release mechanism of the first embodiment shown in FIGS. 2-5. However, it is intended within the scope of the present invention that embodiments of injector devices with release mechanisms are envisaged which comprise a rear cap moveable from an extended position to a depressed position, as with the sixth embodiment shown in FIGS. 15-19, but with features of the release mechanism of the sixth embodiment replaced with features of the release mechanisms of any of the second to fourth embodiments described above and shown in FIGS. 6-7, 8-10 and 11-13 respectively. In such alternative envisaged embodiments, the various different release mechanisms would be actuated by movement of the rear cap from the extended position to the depressed position.

Such cooperating locking arms and recesses may advantageously be evenly spaced around the circumference of the housing 21 and piston rod 24 in order to help towards providing a stable locking position and release movement of the release mechanism.

The embodiments of injector devices described herein are configured to receive either a cartridge of medicament or a syringe pre-filled with a medicament. Herein, the term "medicament container" is intended to encompass both a cartridge of medicament and a pre-filled syringe.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 vamino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injector device comprising:
   an elongate housing having a proximal end and a distal end, the housing being configured to receive a container of medicament;
   a needle sleeve mounted within the housing and movable between an extended position in which the needle sleeve at least partially extends from the distal end of the housing, and a retracted position in which the needle sleeve is received further within the housing than in the extended position;
   a piston rod movable longitudinally within the housing;
   a piston spring configured to bias the piston rod towards the distal end of the housing to engage the container of medicament when received within the housing; and
   a release mechanism configured to control actuation of the piston rod, the release mechanism comprising a locking arm movable between a locked position in which the locking arm is in cooperating engagement with the piston rod and prevents movement of the piston rod, and a release position in which the locking arm is out of engagement with the piston rod so that the piston rod is free to move longitudinally within the housing; and
   wherein the needle sleeve is configured such that movement of the needle sleeve from the extended position to the retracted position causes the locking arm to move from the locked position to the release position.

2. The injector device according to claim 1, wherein the locking arm is configured to pivot between the locked position and the release position.

3. The injector device according to claim 1, wherein the piston rod comprises a recess within which an end of the locking arm is received when the locking arm is in the locked position.

4. The injector device according to claim 1, wherein the release mechanism comprises a securing member which engages the locking arm in the locked position and prevents movement of the locking arm into the release position.

5. The injector device according to claim 4, wherein the release mechanism is configured such that a contact portion of the release mechanism engages the securing member as the needle sleeve moves to the retracted position and moves the securing member out of engagement with the locking arm to allow the locking arm to move into the release position.

6. The injector device according to claim 4, wherein the securing member comprises a deflectable post which is deformed out of engagement with the locking arm when the needle sleeve is moved from the extended position to the retracted position.

7. The injector device according to claim 1, wherein the release mechanism comprises a contact portion configured to engage the locking arm as the needle sleeve moves to the retracted position and moves the locking arm from the locked position to the release position.

8. The injector device according to claim 1, wherein the locking arm is configured to rotate about an axis extending in a longitudinal direction of the housing between the locked position and the release position.

9. The injector device according to claim 1, wherein the locking arm extends inwardly from a lateral side wall of the housing.

10. The injector device according to claim 9, wherein the locking arm comprises a slot within which a portion of the needle sleeve is received when the needle sleeve is in the extended position to prevent movement of the locking arm from the locked position, and wherein the needle sleeve is configured such that movement of the needle sleeve to the retracted position renders the needle sleeve out of engagement with the slot to allow the locking arm to move to the release position.

11. The injector device according to claim 1, further comprising the container of medicament received within the housing between the piston rod and the distal end of the housing.

12. An injector device comprising:
    an elongate housing having a proximal end and a distal end, the housing being configured to receive a container of medicament;
    a rear cap mounted to the proximal end of the housing and movable between an extended position in which the rear cap at least partially extends from the proximal end of the housing, and a depressed position in which the rear cap is received further within the housing than in the extended position;
    a piston rod movable longitudinally within the housing;
    a piston spring configured to bias the piston rod towards the distal end of the housing to engage the container of medicament when received within the housing; and
    a release mechanism configured to control actuation of the piston rod, the release mechanism comprising a locking arm mounted on the rear cap and movable between a locked position in which the locking arm is in cooperating engagement with the piston rod and prevents movement of the piston rod, and a release position in which the locking arm is out of engagement with the piston rod so that the piston rod is free to move longitudinally within the housing; and
    wherein the rear cap is configured such that movement of the rear cap from the extended position to the depressed position causes the locking arm to move from the locked position to the release position.

13. The injector device according to claim 12, wherein the locking arm is configured to pivot between the locked position and the release position.

14. The injector device according to claim 12, wherein the piston rod comprises a recess within which an end of the locking arm is received when the locking arm is in the locked position.

15. The injector device according to claim 12, wherein the release mechanism comprises a securing member which engages the locking arm in the locked position and prevents movement of the locking arm into the release position.

16. The injector device according to claim 15, wherein the release mechanism is configured such that a contact portion of the release mechanism engages the securing member as the rear cap moves to the depressed position and moves the securing member out of engagement with the locking arm to allow the locking arm to move into the release position.

17. The injector device according to claim 15, wherein the securing member comprises a deflectable post which is deformed out of engagement with the locking arm when the rear cap is moved from the extended position to the depressed position.

18. The injector device according to claim 12, wherein the release mechanism comprises a contact portion configured to engage the locking arm as the rear cap moves to the depressed position and moves the locking arm from the locked position to the release position.

19. The injector device according to claim 18, wherein the locking arm is configured to rotate about an axis extending in a longitudinal direction of the housing between the locked position and the release position.

20. The injector device according to claim 12, wherein a support post extends into the housing from the rear cap and the locking arm is moveably connected to the support post.

21. The injector device according to claim 12, further comprising a container of medicament received within the housing between the piston rod and the distal end of the housing.

22. The injector device according to claim 12, wherein the locking arm is movable relative to the rear cap.

23. A method of operating an injector device, the method comprising:
  positioning the injector device relative on an injection site; and
  moving a rear cap or a needle sleeve of the injector device from an extended position to a retracted position or a depressed position, respectively, thereby causing a locking arm of a release mechanism of the injector device to move from a locked position to a release position, wherein in the locked position the locking arm is in cooperating engagement with a piston rod of the injector device and prevents movement of the piston rod, and wherein in the release position, the locking arm is out of engagement with the piston rod so that the piston rod is free to move longitudinally within a housing of the injector device.

* * * * *